United States Patent [19]
Killer

[11] 3,988,591
[45] Oct. 26, 1976

[54] PHOTOMETRIC METHOD FOR THE QUANTITATIVE DETERMINATION OF A MATERIAL OR SUBSTANCE IN AN ANALYSIS SUBSTANCE AND PHOTOELECTRIC PHOTOMETER FOR THE PERFORMANCE OF THE AFORESAID METHOD

[75] Inventor: Walter Heinz Peter Killer, Allschwil, Switzerland

[73] Assignee: Dr. W. Killer AG, Switzerland

[22] Filed: June 2, 1975

[21] Appl. No.: 583,341

[30] Foreign Application Priority Data
June 10, 1974 Switzerland............... 7890/74

[52] U.S. Cl.............................. 250/565; 250/575; 250/576; 356/36; 356/206; 356/208
[51] Int. Cl.[2]................................ G01N 21/24
[58] Field of Search.................. 250/565, 575, 576; 356/36, 179, 205, 206, 229, 243, 39, 208

[56] References Cited
UNITED STATES PATENTS

| | | | |
|---|---|---|---|
| 3,703,336 | 11/1972 | Rosse et al................. | 356/205 X |
| 3,752,995 | 8/1973 | Liedholz..................... | 250/565 X |
| 3,843,265 | 10/1974 | Egli et al..................... | 250/565 X |

*Primary Examiner*—Eugene La Roche
*Attorney, Agent, or Firm*—Ladas, Parry, Von Gehr, Goldsmith & Deschamps

[57] ABSTRACT

A photometric method and photoelectric photometer for the quantitative determination of a substance or material in an analysis substance, wherein the course of the calibration curve representing the functional dependency of an optical measurement magnitude upon the concentration of the substance can be at least approximately determined by at most a number of few parameters. For a calibration curve parameter there is provided a reference sample which contains the substance to be analyzed in a known or unknown concentration. A partial quantity is removed from the analysis substance to serve as the analysis sample and there are formed from further partial quantities of the analysis substance corresponding to the number of further calibration curve parameters calibration samples by the addition of predetermined graduated quantities of the substance to be analyzed to the partial quantities of the analysis substance, so that each calibration sample contains the material to be analyzed in a concentration which is composed of the unknown proportion and a known proportion. The analysis sample, the reference sample and the calibration sample(s) are illuminated and for all samples there are at least approximately simultaneously determined the values of the optical measurement magnitudes, and by means of the measurement magnitude values there is mathematically determined from the course of the calibration curve determined by such measurement magnitude values and the known concentration of the material to be analyzed in the reference sample the concentration of the material or substance in the analysis sample.

11 Claims, 2 Drawing Figures

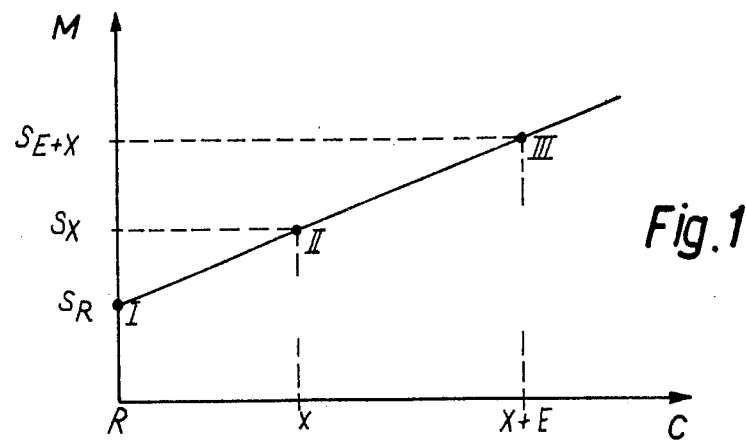
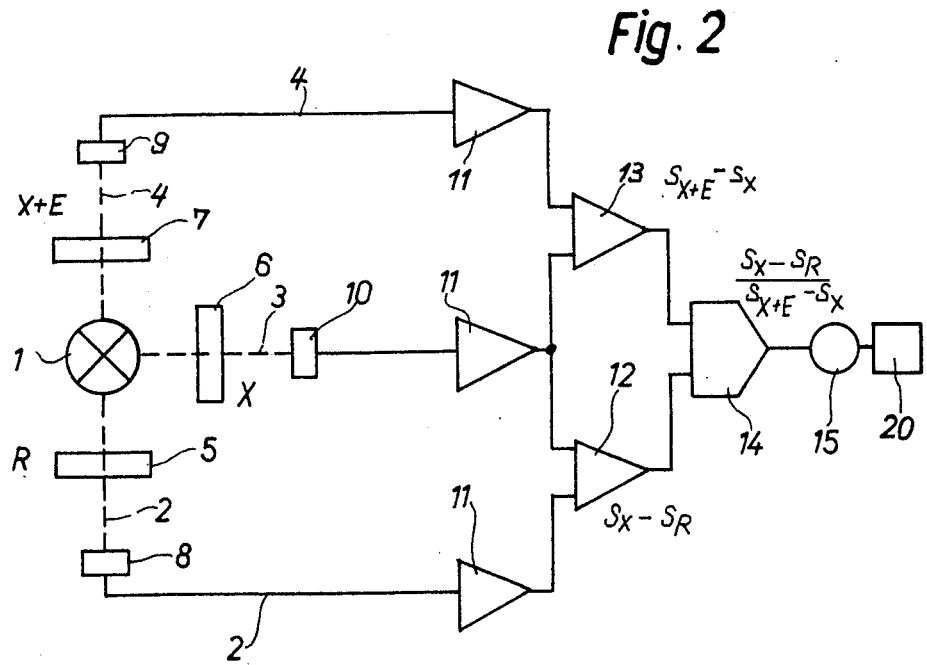

PHOTOMETRIC METHOD FOR THE QUANTITATIVE DETERMINATION OF A MATERIAL OR SUBSTANCE IN AN ANALYSIS SUBSTANCE AND PHOTOELECTRIC PHOTOMETER FOR THE PERFORMANCE OF THE AFORESAID METHOD

BACKGROUND OF THE INVENTION

The present invention relates to a new and improved photometric method for the quantitative determination of a substance or material in an analysis substance, wherein the course of the calibration curve representative of the functional dependency of an optical measurement magnitude or value upon the concentration of the substance can be at least approximately determined by at most several of few parameters, and this invention further pertains to a new and improved construction of photoelectric photometer for the performance of the aforesaid method.

With the heretofore known photometric measurement techniques for the determination of the concentration of a substance or material, for instance in a liquid mixture, there is plotted a calibration curve of the relevant mixture by means of standard-calibration solutions. To determine the concentration there is then measured at spaced time intervals the analysis sample as well as the calibration solution and from the measurement results or values there is determined with the aid of the calibration curve the unknown substance concentration. If the substance or material to be analyzed is not light-absorbing or absorbs light only to a slight extent, then such material is reacted with a specific reagent, so that the resultant product possesses light-absorption properties in a predetermined spectral range or fluorescence, and the degree of transmissibility or absorption of the mixture and the intensity of the fluorescence, respectively, constitute optical measurement magnitudes or values for the determination of the concentration. A prerequisite for the usability of such quantitative photometric analysis is that at least for a longer period of time the optical measurement magnitude is a predetermined and clear function of the concentration of the material or substance. Consequently, the field of use of the photometric determination is rather limited and several chemical processes cannot rely upon such photometric techniques, such as, for instance, precipitation processes wherein the calibration curve is dependent upon the momentarily prevailing size of flakes or flocks (formation of flakes) and different optical parameters.

SUMMARY OF THE INVENTION

Hence, it is a primary object of the present invention to provide an improved photometric method of, and apparatus for, the quantitative determination of a material in an analysis substance in a manner not associated with the aforementioned drawbacks and limitations of the prior art.

Another and more specific object of this invention aims at a new and improved photometric measuring technique which is considerably less limited in its field of application, and also concerns a new and improved construction of photoelectric photometer for the performance of the aforesaid method.

Now in order to implement these and still further objects of the invention, which will become more readily apparent as the description proceeds, the inventive photometric method for the quantitative determination of a substance or material in an analysis substance is manifested by the features that there is provided for a calibration curve parameter a reference sample which contains the substance to be analyzed in a known or unknown concentration, there is removed from the analysis substance a partial quantity serving as the analysis sample and from further partial quantities of the analysis substance there are produced calibration samples, corresponding to the number of further calibration curve parameters, by the addition of predetermined calibrated quantities of the substance to be analyzed to the partial quantities of the analysis substance, so that each calibration sample contains the substance to be analyzed in a concentration which is composed of the unknown proportion and a known proportion. The analysis sample, the reference sample and the calibration sample(s) are illuminated and for all of the samples there is at least approximately simultaneously determined the values of the optical measurement magnitudes, and by means of the measurement magnitude values from the course of the calibration curve determined therefrom and the known concentration of the substance to be analyzed in the reference sample there is mathematically or analytically determined the concentration of the substance in the analysis sample.

The photoelectric photometer for the performance of the aforesaid method aspects as contemplated by the invention is manifested by the features that are provided at least three photometric beam systems which are especially illuminated by a common light source, the beam systems being equipped with a photoelectric measurement value transmitter. One of the beam systems is provided for the detection of the reference sample and for obtaining a reference signal, another of the beam systems is provided for the detection of the analysis sample and for obtaining a sample signal, and each further beam system is provided for the detection of a calibration sample and for obtaining a calibration signal determining one point of the calibration curve. Further, a computer is operatively connected with the measurement value transmitter.

It is not necessary for the reference sample to contain in every instance the substance to be analyzed, it can also contain as far as such substance is concerned the same in a null concentration, for instance, when the substance to be analyzed is only present in a small concentration in the analysis substance. At the photoelectric photometer the photometric beam systems can be constructed for undertaking optical transmission- or absorption measurements, reflection measurements, stray light measurements, fluorescence measurements or turbidimetry measurements. At the computer there can be operatively connected an indicator device for the indication of the computer result in concentration units or also a regulation device for controlling a process as a function of the concentration of the substance in the analysis sample.

BRIEF DESCRIPTION OF THE DRAWING

The invention will be better understood and objects other than those set forth above, will become apparent when consideration is given to the following detailed description thereof. Such description makes reference to the annexed drawing wherein:

FIG. 1 schematically illustrates a calibration diagram or graph wherein there is plotted the optical measurement values or magnitudes M as a function of the concentration C; and FIG. 2 schematically illustrates a circuit diagram of the construction of a photoelectric photometer designed according to the invention possessing three photometric beam systems and a computer which has been represented in block circuit diagram.

DETAILED DESCRIPTION OF THE INVENTION

Referring now to the drawing, in the measurement magnitudes-concentrations-graph of FIG. 1 there is illustrated a calibration line along which there are indicated three points I, II and III which are determined by samples having different concentration of a substance to be analyzed or examined. The first point I which is here located at the measurement magnitude or value coordinate M is determined by the reference sample having the substance concentration null and fixes the position of the calibration line at the coordinate axes. The second point II is determined by the analysis sample with the unknown substance concentration X. The third point III is determined by a calibration sample, which consists of a partial quantity of the analysis substance and an additional predetermined quantity of the substance to be analyzed, so that in the calibration sample the concentration of the substance to be analyzed is composed of the unknown quantity or proportion X of the analysis sample and a known proportion E, i.e., amounts to X + E. As concerns the measurement magnitude values there are present electrical signals, which here have been designated correspondingly as reference signal $S_R$, sample signal $S_X$ and calibration signal $S_{X+E}$. The slope $s$ of the calibration line is determined by the following equation:

EQUATION (1)

$$s = \frac{S_X - S_R}{X} = \frac{S_{X+E} - S_X}{E}$$

wherein, reference character E designates the known concentration proportion in the calibration sample and reference character X designates the unknown concentration in the analysis sample.

From the slope $s$ of the calibration line and its point of intersection determined by the reference signal $S_R$ with the measurement magnitude axis there can be derived the unknown concentration X of the substance to be analyzed in the analysis sample by the means of the following equation:

EQUATION (2)

$$X = \frac{S_X - S_R}{S_{X+E} - S_X} E$$

If in the reference sample the substance to be analyzed is present in a known concentration, which is preferably smaller than in the analysis sample, then the concentration X of the substance to be analyzed in the analysis sample can be determined by the following equation:

EQUATION (3)

$$X = R + ( \frac{S_X - S_R}{S_{X+E} - S_X} E ),$$

wherein, reference character R designates the concentration of the substance to be analyzed in the reference sample.

It should be apparent that the fabrication of the reference sample and the calibration sample in practice is not associated with any difficulties and the construction of the computer can be very simple.

FIG. 2 schematically illustrates the construction of a photoelectric photometer for transmission measurements, which can be used for all analysis substances with a straight line as the calibration characteristic line.

The photometer will be seen to contain a light source 1 and encompasses three photometric beam systems 2, 3, 4 which, in known manner, are constructed for transmission measurements and each contain a respective measurement cuvette or vessel 5, 6, 7 and a photoelectric measurement value transmitter 8, 9, 10. operatively connected with each measurement value transmitter 8, 9, 10 is a respective analogue amplifier 11. Both of the differential amplifiers 12, 13 connected in circuit with the analogue amplifiers 11, as shown, deliver the output signals $S_X - S_R$ and $S_{X+E} - S_X$, which in turn are delivered to an operational amplifier 14. The operational amplifier 14 generates the output signal $(S_X - S_R) (S_{X+E} - S_X)$. Reference character 15 designate summarily structural units, such as computer means, by means of which the output signal of the operational amplifier 14 can be evaluated in any desired manner. Thus, for instance, the unit 15 can signify for example an amplifier having a gain or amplification factor which can be adjusted to the value E in order to carry out the calculations according to Equation (2). Moreover, the structural unit 15 can contain an addition element for carrying out the mathematical or analytical operations according to Equation (3), comparators, threshold value circuits and so forth. The computer 15 furthermore can also be equipped with an electronic mechanism for the correction of possible non-linearities which are particularly caused by the equipment. At the output of the structural unit 15 there can be connected an analogue or digital indicator device, a recorder or printer, a telemetric system or other suitable or equivalent structure, as generally indicated by reference character 20. The photometer can also be used for controlling chemical processes, and thus conceptually the device 20 can be considered to constitute a regulation device for controlling a process as a function of the substance concentration in the analysis sample.

With non-linear function of the optical measurement magnitudes or values from the concentration of the substance to be analyzed there are provided further photometric beam systems for the detection or taking-up of a corresponding large number of calibration samples of different calibration concentrations until there are determined all parameters of the calibration curves.

The decisive advantage in contrast to conventional photometric measuring or measurement techniques and the known photometers resides in the features that the calibration curve in each case can be simultaneously determined together with the concentration determination, and owing to the simple production of the calibration samples, for the fabrication of which and the measuring operation there is required only a relatively small amount of time, so that it is possible to also detect changing processes, provided that the calibration curve does not appreciably change during such preparation- and measuring time.

The previously described photometric measuring or measurement method can thus be employed throughout a considerably larger range than the conventional measuring processes. Thus, it is especially suitable for all substances with which there can be obtained a precipitate or a color reaction or fluorescence, for insoluble substances, which can be determined turbidimetrically or by light scattering, for colloidal systems and for processes which influence the light transmission in a cuvette or vessel.

The photoelectric photometer for the performance of the photometric measurement method or process of this development can be, of course, modified as will be apparent to those skilled in the art, from the purely exemplary embodiment of equipment disclosed above. Thus, for instance, the photoelectric measurement value transmitter or measurement value transmitter arrangement, instead of having a respective separate measurement value transmitter for each bundle of light rays or light beams, can contain a single measurement value transmitter for all light beams and a chopper device or equivalent structure by means of which the measurement value transmitter can be rapidly placed into operation in the individual light beams or the individual light beams or rays can be successively switched into operable association with the measurement value transmitter, such switching operation occurring so rapidly that the successive measurement values are practically simultaneously obtained in consideration of possible variations in the analysis substance.

While there is shown and described present preferred embodiments of the invention, it is to be distinctly understood that the invention is not limited thereto, but may be otherwise variously embodied and practiced within the scope of the following claims.

Accordingly, what is claimed is:

1. A photometric method for the quantitative determination of a substance in an analysis substance, wherein the course of the calibration curve representative of the functional dependency of an optical measurement magnitude upon the construction of the substance can be determined by at most a few parameters, comprising the steps of: providing a reference sample for a calibration curve parameter, said reference sample containing the substance to be analyzed in a known concentration wherein said concentration may be zero or greater, removing from the analysis substance a partial quantity to serve as an analysis sample, and producing from further partial quantities of the analysis substance at least one calibration sample of a different concentration than the reference sample, the calibration samples produced corresponding to the number of further calibration curve parameters by the addition of predetermined graduated quantities of the substance to be analyzed to the partial quantities of the analysis substance whereby the calibration samples have a higher concentration of the substance to be analyzed than the reference sample, each calibration sample thereby containing the substance to be analyzed in a concentration which is composed of the unknown proportion and a known proportion, illuminating the analysis sample, the reference sample and the calibration sample (s), and at least approximately simultaneously determining for all samples the values of the optical MEASUREMENT magnitudes, and mathematically determining the concentration of the substance in the analysis sample from the course of the calibration curve determined by the measurement magnitude values and the known concentration of the substance to be analyzed in the reference sample.

2. A photoelectric photometer for the quantitative determination of a substance in an analysis substance, comprising at least three photometric beam systems illuminated from a common light source, a means including one of said beam systems for detecting a reference sample and for obtaining a reference signal, a means including another of said beam systems for detecting an analysis sample and for obtaining a sample signal, a means including each further beam system for detecting a calibration sample and for obtaining a calabration signal determining a point on a calabration curve, each of said means further including photoelectric measurement value transmitter means operatively associated with the light source and each of said illuminated beam systems, and a computer operatively connected with said measurement value transmitter means so as to receive said signals.

3. The photoelectric photometer as defined in claim 2, further including an indicator device operatively connected with the computer for indicating the computer result in concentration units.

4. The photoelectric photometer as defined in claim 2, wherein the photometric beam systems are designed for optical transmission measurements.

5. The photoelectric photometer as defined in claim 2, wherein the photometric beam systems are designed for absorption measurements.

6. The photoelectric photometer as defined in claim 2, wherein the photometric beam systems are designed for optical reflection measurements.

7. The photoelectric photometer as defined in claim 2, wherein the photometric beam systems are designed for stray light measurements.

8. The photoelectric photometer as defined in claim 2, wherein the photometric beam systems are designed for carrying out fluorescence measurement.

9. The photoelectric photometer as defined in claim 2, wherein the photometric beam systems are designed for turbidimetric measurements.

10. The photoelectric photometer as defined in claim 2, wherein said photometric beam systems illuminated by a common light source are utilized for analysis substances possessing at least approximately linear calibration curves, the reference signal and the known substance concentration in the reference sample determining a reference point of the linear calibration curve, and wherein from the difference of the calibration signal and the sample signal and the known concentration proportion of the substance in the calibration sample and the known concentration of the substance in the reference sample there is determined the slope of the linear calibration curve, and wherein said computer which is connected with the photoelectric measurement value transmitter means delivers an output signal which is indicative of the concentration of the substance in the analysis sample.

11. The photoelectric photometer as defined in claim 10, wherein said photoelectric measurement value transmitter means comprises at least three photoelectric measurement value transmitters, each of said photoelectric measurement value transmitters being operatively associated with one of said beam systems, two differential amplifiers connected in circuit with said computer, one of said differential amplifiers being connected with the photoelectric measurement value transmitters of the beam system provided for obtaining the sample signal and the beam system provided for obtaining the reference signal, and the other differential amplifier being connected with the photoelectric measurement value transmitters of the beam system provided for obtaining the sample signal and the beam system provided for obtaining the calibration signal, in order to thereby obtain appropriate differential signals, said differential ampifiers having outputs at which there is connected an operational amplifier for division operations in order to obtain an output signal proportional to the quotient of the input signals, said output signal indicating the relationship of the unknown substance concentration in the analysis sample to the known substance concentration in the calibration sample.

* * * * *